United States Patent [19]

Bluthe et al.

[11] Patent Number: 4,942,240
[45] Date of Patent: Jul. 17, 1990

[54] PREPARATION OF AROMATIC ALDEHYDES

[75] Inventors: Norbert Bluthe, Villeurbanne; Robert Perron, Charly, both of France

[73] Assignee: Rhone-Poulenc Chimie, Courbevoie, France

[21] Appl. No.: 43,363

[22] Filed: Apr. 28, 1987

[30] Foreign Application Priority Data

Apr. 28, 1986 [FR] France ................................. 86 06363

[51] Int. Cl.$^5$ ..................... C07C 45/49; C07D 213/02
[52] U.S. Cl. ................................... 546/298; 546/296; 546/299; 546/314; 546/315; 568/428
[58] Field of Search ................ 568/428; 546/290, 286, 546/287, 288, 296, 298, 299, 314, 315

[56] References Cited

U.S. PATENT DOCUMENTS

| | | | |
|---|---|---|---|
| 3,960,932 | 6/1976 | Heck | 560/144 |
| 4,536,344 | 8/1985 | Fiedler et al. | 546/314 |
| 4,605,749 | 8/1986 | Buchman | 546/314 |

*Primary Examiner*—Richard A. Schwartz
*Assistant Examiner*—Zinna Northington-Davis
*Attorney, Agent, or Firm*—Burns, Doane, Swecker & Mathis

[57] ABSTRACT

Aromatic aldehydes are more rapidly produced by reacting hydrogen/carbon monoxide admixture with an aromatic halide in the presence of a noble metal-based catalyst, a tertiary nitrogenous base and, if necessary, a noble metal complexing agent, e.g., a phosphine or phosphite, wherein the concentration of said tertiary nitrogenous base, expressed in moles per liter of reaction mixture, is maintained at a value of at least two moles/liter over the course of the reaction.

15 Claims, No Drawings

PREPARATION OF AROMATIC ALDEHYDES

CROSS-REFERENCE TO RELATED APPLICATION

Our copending application Ser. No. 07/043,423, filed concurrently herewith and assigned to the assignee hereof.

BACKGROUND OF THE INVENTION

1. Field of the Invention

The present invention relates to the preparation of aromatic aldehydes, and, more especially, to the preparation of aromatic aldehydes by the hydrocarbonylation of aromatic halides in the presence of a noble metal, a tertiary nitrogenous base and, where necessary, a phosphorus compound.

2. Description of the Prior Art

A process for the preparation of aldehydes by reacting a gaseous mixture of hydrogen and carbon monoxide with an organic halide of the group consisting of aromatic, vinyl and heterocyclic halides in the presence of a tertiary amine and a palladium catalyst which consists of a complex of a divalent palladium derivative with a phosphine (triphenylphosphine), a phosphite or an arsine, or of the combination of a divalent palladium salt (acetate or chloride) or finely divided palladium metal with a phosphine, phosphite or arsine complexing agent, is described in U.S. Pat. No. 3,960,932. In the latter case, the ratio of the number of g-at. of P to the number of g-at. of Pd may be between 0.5 and 5. The reaction is carried out at a temperature of 75° C. to 175° C. and at a pressure of 7 to 140 bar. In general, the nitrogenous base is used in slight excess compared with the theoretical amount required for the neutralization of the hydracid which is a byproduct of the reaction. This process is particularly well suited for the preparation of aromatic aldehydes by the hydrocarbonylation of the corresponding bromides. In spite of the good results obtained, this process suffers from a serious disadvantage in the time periods required for reaction, i.e., periods on the order of 10 to 26 hours. These reaction times result in low productivities of the equipment and negate any industrial value of the process.

In order to alleviate the disadvantages of the process described in U.S. Pat. No. 3,960,932, the hydrocarbonylation of aromatic halides at pressures of 20 to 400 bar, at a temperature of 80° to 250° C., in the presence of a noble metal-based catalyst, a tertiary nitrogenous base and a large amount of a phosphine or a phosphite has been proposed. See published European Patent Application No. 0,109,606. The amount of the phosphorus derivative represents from 2 to $10^5$ times the molar amount of the catalyst, preferably from 10 to 1000 times. As it enables the use of high reaction temperatures without degradation of the catalyst, this particular process enables the reaction rate, and, consequently, the productivity of the equipment to be increased. However, the increase in the reaction rate is still considered insufficient and inexorably linked to the use of high temperatures.

Cf. Schoenberg et al, *Journal American Chemical Society*, 96, No. 25, pp. 7761–7764 (Dec. 11, 1974); EP-A-No. 0,165,881.

SUMMARY OF THE INVENTION

Accordingly, a major object of the present invention is the provision of an improved process for the preparation of aromatic aldehydes, characterized by an increased rate of reaction, preferably without having to resort to high reaction temperatures. Indeed, from thorough consideration and detailed analysis of the totality of the reaction parameters, it has now been determined that the concentration of the tertiary nitrogenous base has a marked effect on the reaction rate. More particularly, it has now unexpectedly been determined that the reaction rate is positive in relation to the nitrogenous base, which means that above a certain concentration of the base, the reaction rate is independent of this concentration. By the term "nitrogenous base concentration" as utilized herein, there is intended the number of moles of base per liter of the reaction mixture including the base, the aromatic halide, and, where appropriate, the organic solvent or diluent.

Briefly, the present invention features a process for preparing aromatic aldehydes by reacting a hydrogen/carbon monoxide mixture with an aromatic halide, namely, bromide or iodide, in the presence of a noble metal-based catalyst, a tertiary nitrogenous base and, if required, a noble metal complexing agent selected from among the phosphines and phosphites, wherein the concentration of nitrogenous base, expressed in moles per liter of reaction mixture, is maintained at a value of at least 2 moles/liter throughout the reaction period.

DETAILED DESCRIPTION OF THE PREFERRED EMBODIMENTS OF THE INVENTION

More particularly according to the present invention, the concentration of the nitrogenous base is preferably maintained at at least 2.5 moles per liter during the reaction The various reaction conditions are those described in the '932 patent and the '606 patent application noted above.

To carry out the process according to the invention, a finely divided noble metal of Group VIII of the Periodic Table of elements, such as palladium, rhodium or iridium, or their inorganic or organic acid salts or their complexes with electronic pair donor compounds, especially their complexes with phosphines, phosphites or arsines, are advantageously used as catalysts. Palladium derivatives are particularly well suited for implementing the process according to the invention. As specific examples of such palladium derivatives, representative are palladium (II) carboxylates (acetate, propionate, butyrate and benzoate), palladous chloride and palladium complexes of the general formulae $PdX_2[P(R)_3]_2$ or $PdX_2[P(OR)_3]_2$, in which X represents a halogen (bromine, chlorine) atom or an inorganic or carboxylic acid residue and R represents a hydrocarbon radical. Dichlorodi(triphenylphosphino)palladium (II) and dibromodi(tritolylphosphino)palladium (II) are especially noteworthy.

The amount of catalyst, expressed as gram-atoms of metal or as moles of metal derivative per mole of aromatic halide, may vary over wide limits. Thus, it may range from $10^{-5}$ to $10^{-1}$ g-at. or moles per mole, and preferably from $10^{-4}$ to $10^{-2}$ g-at. or moles per mole.

Exemplary of the tertiary nitrogenous base, amines of the following general formula are representative

in which the $R_1$ radicals, which may be identical or different, represent hydrocarbon radicals containing from 1 to 20 carbon atoms, such as alkyl, cycloalkyl or aryl radicals. The symbols $R_1$ are preferably alkyl radicals containing from 1 to 10 carbon atoms or cycloalkyl radicals containing from 5 to 10 carbon atoms. Triethylamine, tri-n-propylamine, tri-n-butylamine, methyldibutylamine, methyldicyclohexylamine and ethyldiisopropylamine are specific examples of such bases. Heterocyclic tertiary amine bases such as pyridine and picolines may also be used.

The amount of base must be sufficient both for neutralizing the hydracid released by the reaction and such that the base concentration is at least 2 mols per liter of the reaction mixture throughout the reaction period. When these two conditions are satisfied, there is no critical upper limit for the amount of the base, which can be used in a large excess compared with that amount theoretically required for the neutralization of the hydracid formed. In order to maintain the concentration of the base at least equal to the limiting values given above throughout the period of the reaction, the amount of base must be calculated such that, upon completion of the reaction, the concentration of the base is at least equal to these values. An additional amount of base may also be added as the reaction proceeds, such as to compensate for that amount consumed by the neutralization of the hydracid.

The phosphines and phosphites which are suitable for carrying out the subject reaction are those noted in the U.S. Pat. No. 3,960,932 or in European Patent Application No. 0,109,606, hereby incorporated by reference. Exemplary of these compounds, representative are: triphenylphosphine, triphenylphosphite, diethylphenylphosphine, diethylphenylphosphite, tritolylphosphine, tritolylphosphite, trinaphthylphosphine, trinaphthylphosphite, diphenylmethylphosphine, diphenylmethylphosphite, diphenylbutylphosphine, diphenylbutylphosphite, tris(p-methoxycarbonylphenyl)phosphine, tris(p-methoxycarbonylphenyl)phosphite, tris(p-cyanophenyl)phosphine, tris(cyanophenyl)phosphite, triethylphosphite, tributylphosphine and tributylphosphite.

The presence of a free phosphorus-containing complexing agent in the reaction medium depends on the nature of the catalyst and/or the reaction conditions. When the catalyst is a complex of a noble metal with a phosphine or a phosphite, the presence of the latter in free state is not indispensable. However, it proves advantageous when the reaction is carried out at a high temperature, for example at a temperature greater than 150° C. When a noble metal is employed in the metallic state or as a derivative which is not complexed with a phosphine or a phosphite, such as, for example, noble metal carboxylates, it is essential to carry out the reaction in the presence of the phosphorus-containing compound. When the reaction is carried out in the presence of a phosphite or a phosphine, the amount thereof is selected such that the ratio of the number of gram-atoms of phosphorus (P) to the number of gram-atoms of metal (M) is at least equal to 2. The ratio P/M may have values as high as 10,000. A P/M ratio of from 5 to 1,000 is typically suitable.

The process according to the invention is particularly well suited for the preparation of aromatic aldehydes having the general formula:

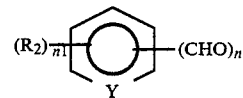

in which:

$n$ is 1 or 2;

$n_1$ is an integer of from 1 to 4; and $R_2$ represents: a hydrogen, fluorine or chlorine atom; an alkyl radical which may be substituted, if required, with one or more chlorine and/or fluorine atoms; cycloalkyl; aryl; alkoxy; cycloalkoxy; aryloxy; alkoxycarbonyl; cycloalkoxycarbonyl; aryloxycarbonyl; alkyl-, cycloalkyl- or arylcarbonyloxy radical, optionally substituted with one or more fluorine and/or chlorine atoms; a nitrile group; or, when $n_1$ is equal to 2, two $R_2$ radicals borne by neighboring carbon atoms which form a hydrocarbon ring or a heterocycle with the latter.

When $n_1$ is greater than 1, the different substituents $R_2$ may be identical or different.

Y represents a divalent radical —CH— or a nitrogen atom.

In the formula (I), $R_2$ preferably represents:

(i) straight or branched chain alkyl radicals containing from 1 to 20 carbon atoms, such as methyl, ethyl, propyl, butyl, pentyl, 2-ethylhexyl, trifluoromethyl, difluorochloromethyl, trichloromethyl and decyl radicals. $R_2$ more preferably represents a lower alkyl radical (containing from 1 to 4 carbon atoms);

(ii) cycloalkyl radicals containing from 5 to 10 carbon atoms, such as cyclopentyl, cyclohexyl and cyclooctyl;

(iii) phenyl radicals which may be substituted, if required, with one or more lower alkyl or lower alkoxy radicals, such as phenyl, xylyl, tolyl, methoxyphenyl and ethoxyphenyl;

(iv) alkoxy radicals containing from 1 to 20 carbon atoms, preferably from 1 to 10 carbon atoms, such as methoxy, ethoxy, isopropyloxy, butoxy, trifluoromethoxy, difluorochloromethoxy and trichloromethoxy;

(v) alkoxycarbonyl radicals containing from 1 to 10 carbon atoms in the alkoxy residue, preferably lower alkoxycarbonyl radicals such as methoxy-, ethoxy-, isopropyloxy- and butyloxycarbonyl;

(vi) cycloalkoxycarbonyl radicals containing from 5 to 10 carbon atoms, such as cyclopentyloxycarbonyl and cyclohexyloxycarbonyl;

(vii) phenyloxycarbonyl and tolyloxycarbonyl radicals;

(viii) alkylcarbonyloxy radicals containing from 1 to 10 carbon atoms, such as acetoxy, propionyloxy and butyroyloxyl;

(ix) cycloalkylcarbonyloxy radicals containing from 5 to 10 carbon atoms, such as cyclopentanoyloxy and cyclohexanoyloxy;

(x) benzoyloxy, methylbenzoyloxy and dimethylbenzoyloxy radicals; and (xi) when two $R_2$ radicals form a ring together with the neighboring carbon atoms from which they depend, this ring may more particularly be a benzene ring which may be substituted, if required, with lower alkyl or alkoxy radicals, or a methylenedioxy ring (1,3-dioxacyclopentane).

As specific examples of aldehydes of the formula (I) which may be prepared by the process of the invention, representative are: benzaldehyde, tolualdehydes, anisaldehydes, vanillin, trimethoxybenzaldehyde, 3,4-methylenedioxybenzaldehyde (piperonal), terephthaldehyde, o-, m- or p-trifluoromethoxybenzaldehydes, o-, m- or p-trichloromethoxybenzaldehydes, o-, m- or p-difluorochloromethoxybenzaldehydes, naphthylaldehydes and formylpyridines.

Exemplary of the aromatic halide starting materials used in the process according to the invention, compounds having the following general formula are illustrative:

(II)

in which n, $n_1$, $R_2$ and Y are as defined above and X represents a bromine or iodine atom. As specific examples of such compounds, representative are: bromobenzene, o-, m- and p-bromotoluenes, 2,3-dimethylbromobenzene, 2,4-dimethylbromobenzene, o-, m- and p-trifluorobenzenes, o, m- and p-fluoroiodobenzenes, 2,3-difluorobromobenzene, o, m- and p-trifluoromethylbromobenzenes, o-, m- and p-trifluoromethyliodobenzenes, trifluoromethoxybromobenzenes, trifluoromethoxyiodobenzenes, o-, m- and p-difluorochloromethylbenzenes, difluorochloromethoxybromobenzenes, bromobenzonitriles, dibromobenzenes, 1-bromonaphthalene, 2-bromopyridine, 4-bromopyridine, p-bromodiphenylether, methyl bromobenzoates, p-bromoanisole, orthobromoanisole, p-bromodiphenylether, methyl bromobenzoates, p-bromoanisole, orthobromoanisole, p-bromophenetole, 3,4-dimethoxybromobenzene, 3,4,5-trimethoxybromobenzene and 3-bromomethylenedioxybenzene.

The temperature at which the process according to the invention is carried out may vary over wide limits. In general, any temperature within the range of from 50° to 250° C. may be used. The temperature preferably ranges from 75° to 200° C.

The total pressure of the hydrogen/carbon monoxide mixture advantageously ranges from 1 to 400 bar and preferably from 10 to 250 bar. The $H_2/CO$ volume ratio may also vary over wide limits. In general, it ranges from 0.1 to 10, and preferably from 0.2 to 5.

The process according to the present invention is carried out in liquid phase. Where appropriate, a solvent which is inert under the conditions of the reaction is used. For this purpose, saturated aliphatic or cycloaliphatic hydrocarbons (hexane, cyclohexane) or aromatic hydrocarbons: benzene, toluene, xylene; esters such as methyl benzoate, methyl terephthalate, methyl adipate, dubutyl phthalate, esters or ethers of polyhydric alcohols such as tetraethyleneglycol diacetate, cyclic ethers (tetrahydrofuran and dioxane) may be used.

From a practical point of view, the process of the invention is carried out simply by introducing the aryl halide, the nitrogenous base, the catalyst and, where appropriate, the phosphorus derivative and a solvent into an inert autoclave and then supplying a $CO/H_2$ mixture into the closed autoclave at a sufficient pressure. The contents of the autoclave are then heated to the appropriate temperature, under stirring, until the absorption of gases ceases. The pressure in the autoclave may be maintained constant during the period of the reaction by connecting it to a reservoir of gaseous mixture at the chosen pressure. Upon completion of the reaction, the contents of the autoclave are cooled, the autoclave is degassed and the reaction mass is filtered to separate the hydrohalide of the nitrogenous base. The filtrate is then distilled in order to separate the organic constituents of the reaction medium. The distillation residue which contains the catalyst may be recycled for use in a new operation.

The process according to the invention may be carried out batchwise or continuously.

In order to further illustrate the present invention and the advantages thereof, the following specific examples are given, it being understood that same are intended only as illustrative and in nowise limitative.

EXAMPLE 1:

The following materials were charged into a 125 ml stainless steel autoclave, purged beforehand with argon:
(i) 5.025 g (25 mmoles) of bromomethylenedioxybenzene (approximately 3 ml);
(ii) 10.1 g (100 mmoles) of triethylamine (approximately 13.9 ml);
(iii) 224 mg of palladium diacetate;
(iv) 1.31 g of triphenylphosphine; and
(v) 20 ml of dibutyl phthalate.

The reactor was closed, agitated by a reciprocating shaking system, heated to 135° C. and connected to a reservoir of 1:1 by volume $CO/H_2$ mixture. The pressure in the autoclave was maintained at 30 bar. The drop in pressure in the reservoir enabled the progress of the reaction to be monitored. It was observed that gas absorption ceased after 1 hr, 40 min, under these conditions. The autoclave was cooled and then degassed, and the reaction mass was analyzed by gas chromatography. It was observed that 3.11 g of piperonal were formed, which represents a yield of 82% relative to the bromomethylenedioxybenzene charged (actual yield of AY). The initial concentration of the base was 2.7 and the final concentration was 2.46.

The initial reaction rate, expressed in mmol gas absorbed per hour, was 80 mmoles $h^{-1}$.

EXAMPLE 2:

Example 1 was repeated by varying the initial concentration of the base in the medium. The results reported in Table I below were obtained:

TABLE I

| Example | Triethyl amine mmols | Concentration of triethylamine Initial mols/l | Concentration of triethylamine Final mols/l | REACTION PERIOD (h) | AY % | Initial rate mmol $h^{-1}$ |
|---|---|---|---|---|---|---|
| 2 | 150 | 3.42 | 3.34 | 1 h, 40 min | 80 | 77 |
| TRIALS | | | | | | |
| A | 30 | 1.1 | 0.24 | 7 h, 30 min | — | 16 |
| B | 55 | 1.8 | 1.24 | 2 h | 82 | 34 |

EXAMPLES 3 and 4:

The reaction was carried out as in Examples 1 and 2 and in trial B, but reducing the amount of catalyst by half (0.5 mmol of palladium diacetate). The results reported in Table II below were obtained:

TABLE II

| Example | mmol | Triethylamine Concentration mol $l^{-1}$ initial | Triethylamine Concentration mol $l^{-1}$ final | Initial rate mmols $h^{-1}$ |
|---|---|---|---|---|
| 3 | 100 | 2.7 | >2.46 | 29 |

TABLE II-continued

| Example | mmol | Triethylamine Concentration mol l$^{-1}$ initial | final | Initial rate mmols h$^{-1}$ |
|---|---|---|---|---|
| 4 | 150 | 3.42 | >3.34 | 27 |
| TRIAL C | 55 | 1.8 | 1.24 | 15 |

It was determined that, irrespective of the amount of the amount of catalyst employed, the concentration of the base had the same effect on the reaction rate.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aromatic aldehyde, comprising reacting hydrogen/carbon-monoxide admixture with an aromatic halide in the presence of a noble metal-based catalyst and a tertiary nitrogenous base, and wherein the concentration of said tertiary nitrogenous base, expressed in moles per liter of reaction mixture, is maintained at a value of at least two moles/liter throughout the reaction period.

2. The process as defined by claim 1, the reaction mixture further comprising a phosphine or phosphite noble metal complexing agent.

3. The process as defined by claims 1 or 2, said aromatic halide comprising an aromatic bromide or iodide.

4. The process as defined by claim 3, wherein the concentration of said tertiary nitrogenous base is at least 2.5 moles/liter.

5. The process as defined by claim 3, for the preparation of an aromatic aldehyde of the following formula:

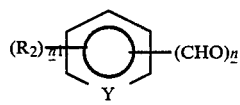

(I)

in which n is 1 or 2; $n_1$ is an integer of from 1 to 4; $R_2$ is a hydrogen, fluorine or chlorine atom, an alkyl radical, an alkyl radical bearing at least one chlorine, fluorine atom substituent or both, a cycloalkyl, aryl, alkoxy, cycloalkoxy, aryloxy, alkoxycarbonyl, cycloalkoxycarbonyl, aryloxycarbonyl, alkyl-, cycloalkyl- or arylcarbonyloxy radical, or a substituted such radical bearing at least one fluorine, chlorine atom substituent or both, a nitrile radical, or, when $n_1$ is equal to 2, two $R_2$ radicals borne by adjacent carbon atoms may together form a hydrocarbon ring or a heterocycle therewith; and Y is a divalent radical —CH— or a nitrogen atom; comprising reacting hydrogen/carbon monoxide admixture with an aryl halide of the general formula:

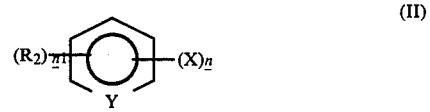

(II)

in which n, $n_1$, $R_2$ and Y are as defined above and X is a bromine or iodine atom.

6. The process as defined by claim 5, wherein the tertiary nitrogenous base is a tertiary amine.

7. The process as defined by claim 5, carried out at a temperature of from 50° to 250° C.

8. The process as defined by claim 5, wherein the total pressure of the hydrogen/carbon monoxide admixture ranges from 1 to 400 bar.

9. The process as defined by claim 5, wherein the H$_2$/CO volume ratio ranges from 0.1 to 10.

10. The process as defined by claim 5, wherein the catalyst comprises palladium metal or a palladium compound.

11. The process as defined by claim 10, wherein the amount of palladium, expressed as gram-atoms of noble metal or as moles of metal compound per mole of aromatic halide, ranges from 10$^{-5}$ to 10$^{-1}$.

12. The process as defined by claim 2, wherein the amount of phosphine or phosphite is such that the ratio of the number of gram-atoms of phosphorus therein to the number of gram-atoms of metal ranges from 1 to 10,000.

13. The process as defined by claim 5, wherein the catalyst comprises a Group VIII noble metal.

14. The process as defined by claim 5, carried out in an inert organic solvent.

15. The process as defined by claim 1, wherein the catalyst comprises a complex of a noble metal with a phosphine or phosphite.

* * * * *